(12) United States Patent
Brar

(10) Patent No.: US 10,105,512 B1
(45) Date of Patent: Oct. 23, 2018

(54) ANTIMICROBIAL CATHETER JACKET

(71) Applicant: Harjeet S. Brar, Bakersfield, CA (US)

(72) Inventor: Harjeet S. Brar, Bakersfield, CA (US)

( * ) Notice: Subject to any disclaimer, the term of this patent is extended or adjusted under 35 U.S.C. 154(b) by 114 days.

(21) Appl. No.: 14/717,932

(22) Filed: May 20, 2015

(51) Int. Cl.
*A61M 25/00* (2006.01)

(52) U.S. Cl.
CPC ..... *A61M 25/0017* (2013.01); *A61M 25/0014* (2013.01)

(58) Field of Classification Search
CPC .............. A61M 25/0017; A61M 25/0014
See application file for complete search history.

(56) References Cited

U.S. PATENT DOCUMENTS

| | | | | |
|---|---|---|---|---|
| 4,475,900 A | * | 10/1984 | Popovich | A61L 2/10 604/28 |
| 4,834,711 A | * | 5/1989 | Greenfield | A61M 25/0111 604/172 |
| 5,334,166 A | | 8/1994 | Palestrant | |
| 5,620,424 A | * | 4/1997 | Abramson | A61M 25/0111 604/174 |
| 5,695,482 A | | 12/1997 | Kaldany | |
| 6,461,569 B1 | | 10/2002 | Boudreaux | |
| 7,931,877 B2 | * | 4/2011 | Steffens | A61L 2/18 134/166 R |
| 7,947,021 B2 | | 5/2011 | Bourne et al. | |
| 2008/0051736 A1 | | 2/2008 | Rioux et al. | |
| 2010/0106103 A1 | * | 4/2010 | Ziebol | A61L 2/186 604/265 |
| 2010/0160880 A1 | * | 6/2010 | Weston | A61M 1/0088 604/319 |
| 2011/0186765 A1 | * | 8/2011 | Jaeb | F16K 99/0015 137/512.1 |
| 2011/0213339 A1 | | 9/2011 | Bak | |

OTHER PUBLICATIONS

Haaland, Carter, "Fellows invent UV catheter sleeve," mndaily.com, Sep. 22, 2009 (US).
Author Unknown, "Medical device infection control system for sterilization of catheter access point with ultraviolet light," Regents of the Univ. of Minnesota, Jun. 25, 2010, US.
Author Unknown, "Ultra-Clean Catheter Site Disinfection System," UVSolutions, Nov. 3, 2011 (US).

* cited by examiner

*Primary Examiner* — Lauren P Farrar
(74) *Attorney, Agent, or Firm* — R. Scott Kimsey, Esq.; Klein DeNatale Goldner

(57) ABSTRACT

An antimicrobial device for use with a catheter includes a jacket having a central opening for receiving a catheter in sliding engagement therewith and an antimicrobial means disposed within the jacket for reducing the number of microbes on the catheter or the skin of the patient. When the catheter is inserted through the central opening of the jacket, the antimicrobial means acts to disinfect the exterior surface of the catheter.

9 Claims, 13 Drawing Sheets

ANTIMICROBIAL CATHETER JACKET

RELATED APPLICATIONS

Not Applicable.

BACKGROUND

1. Field

The present invention relates generally to the field of antimicrobial devices, and more specifically to a device for eliminating or reducing the presence of viable microorganisms on the surface of a hemodialysis catheter and at the site of entry of a hemodialysis catheter into the body of a patient.

2. Background

Infection at the site of a wound is always a serious concern for health care providers, whether due to microorganisms exposed to the patient outside of the healthcare facility or within the healthcare facility, where microorganisms are prevalent. One example of a wound inflicted by the health care provider is that created through the insertion of a hemodialysis catheter. When a patient's kidneys fail and can no longer clean the blood and remove excess fluid from the body, hemodialysis treatments are necessary. In order for hemodialysis to be performed, vascular access is necessary. Hemodialysis catheters are used for this purpose.

Hemodialysis catheters are "tunneled" catheters that are placed at least partially under the skin of a patient. A hemodialysis catheter may be cuffed or non-cuffed, depending on the specific use for the catheter. Non-cuffed catheters are typically used for emergencies, or for short periods of time. By contrast, cuffed catheters can be used for extended periods of time. Hemodialysis catheters include two openings or "lumina," one of which draws blood out of the body and into the dialysis pathway while the other returns cleaned blood to the body.

Because hemodialysis catheters are retained within the body over time, the risk of infection is always cause for concern. Sepsis-related death in dialysis patients has been reported at a rate 100 times greater than in the general population. Follow-up studies of patients with tunneled hemodialysis catheters have shown that 35% of patients develop at least one episode of catheter-related infection within three months of receiving the catheter, and 48% develop at least one infection after six months. Other serious complications that have resulted as a consequence of infection related to hemodialysis catheters include infective endocarditis, septic arthritis, septic emboli, osteomyelitis, epidural abscess, and severe sepsis. At least one of these has been reported in around 20% of patients. In most cases, *S. aureus* is the infective agent.

Infections related to hemodialysis catheters not only pose serious health risks, they are also responsible for significant expense relating to care. A single episode of bacteremia may cost as much as forty-five thousand dollars to treat. As health care costs continue to rise, the costs associated with treating such infections also increases.

Attempts have been made to reduce the risk of infection through the use of antimicrobial catheter coatings, heparin coatings, and the like. Antimicrobial coatings have proven ineffective, as has peri-operative antimicrobial administration (see, for example, "Systematic Review of Antimicrobials for the Prevention of Haemodialysis Catheter-Related Infections," *Nephrol. Dial. Transplant* (2009) 24(12):3763-3774). Heparin-coated catheters have shown a lower frequency of catheter-related bacteremia (see, for example, "Does Heparin Coating Improve Potency or Reduce Infection of Tunneled Dialysis Catheters?" (2009) 4(11):1787-1790), however the incidence of bacteremia and other complications of catheter-related infection remain unacceptably high.

The problems surrounding use of hemodialysis catheters may be applicable to use of any foreign object inserted into a patient's body. The present device addresses such problems in terms of the use of hemodialysis catheters, but the principles set forth herein may be adapted for use with respect to other instruments.

SUMMARY

One embodiment of the present antimicrobial catheter jacket includes a jacket having a central opening in a surface of the jacket. The central opening is sized and shaped to receive a catheter. An antimicrobial means is provided within the jacket to reduce the number of microbes on the external surface of the catheter, on the skin of a patient receiving the catheter, or both. When a catheter is inserted through the central opening of the jacket, the antimicrobial means acts to disinfect the exterior surface of the catheter.

Another aspect of the invention provides an adhesive on a surface of the antimicrobial device that is in contact with the skin of a patient for firmly affixing the antimicrobial device to the skin of the patient.

In another aspect of the invention, the antimicrobial fluid is an antimicrobial gel.

In another aspect of the invention, the jacket includes an injection port that allows antimicrobial fluid to flow into the jacket, but that prevents antimicrobial fluid from flowing out of the jacket. An ejection port is also provided to allow antimicrobial fluid to flow out of the jacket.

In another aspect of the invention, the jacket includes both an inner jacket and an outer jacket extending around the inner jacket. The inner jacket includes an opening for receiving a catheter. The inner jacket includes an injection port to allow antimicrobial fluid to flow into the inner jacket and at least one one-way valve to allow antimicrobial fluid to flow from the inner jacket into the outer jacket. The outer jacket includes an ejection port to allow antimicrobial fluid to flow out of the device.

In another aspect of the invention, an interior space within the inner jacket is in contact with the insertion site of the skin of a patient having a catheter.

In another aspect of the invention, the antimicrobial device includes a flange extending along a perimeter of the device. The flange includes an adhesive for affixing the antimicrobial device to the skin of a patient.

In another aspect of the invention, the inner jacket includes at least one truss to direct the flow of antimicrobial fluid.

In another aspect of the invention, the outer jacket includes at least one truss to direct the flow of antimicrobial fluid.

In another aspect of the invention, the antimicrobial means is an ultraviolet radiation source.

In still another aspect of the invention, the antimicrobial means is a heat source.

Another aspect of the invention provides a device for protecting against antimicrobial infection that includes a semipermeable inflatable membrane, a first inlet tube in fluid communication with the semipermeable membrane, and a semipermeable conduit in fluid communication with the semipermeable membrane. A cover extends over the inflatable membrane and semipermeable conduit and defines an opening for the inlet tube and a central opening for insertion of a catheter therethrough. When an antimicrobial agent is introduced into the semipermeable inflatable membrane, at least a portion of the antimicrobial agent flows into the conduit. The antimicrobial agent is able to flow through the semipermeable membrane and semipermeable conduit to an interior space of the device. The cover may define an opening suitable for insertion of a catheter therethrough, such that an external surface of the semipermeable membrane contacts an external surface of the catheter. An outlet tube may be provided for aspirating an interior space of the device.

Another aspect of the device includes an adhesive flange for affixing the cover to the skin of a patient. The device is airtight when so affixed to a patient's skin so as to maintain a constant desired state within the device over a desired treatment period.

The constant desired state may include any desired gas or combination of gases. The constant desired state may include a vacuum.

The device may also include a vacuum port for creating a vacuum within the interior of the device.

The device may also include an antimicrobial structure, such as a heating element for maintaining a desired temperature of a liquid or gas within the device, an ultraviolet source, an ultrasonic source, or combinations of these.

DETAILED DESCRIPTION

Certain terms used herein refer to the orientation of the present device, or to the top or bottom thereof. As used herein, the word top, and like words, refers to the exterior, convex surface of the cover of the present device, or portions or surfaces of the present device oriented away from the entry site of a catheter into the body of a patient when the present device is in use. This holds true whether the device is oriented so that this surface extends upward, such as when the device is positioned atop a wound on a patient's skin, or when the device is positioned on the underside of a patient's skin. Likewise, the interior, concave surface of the cover of the present device, or portions or surfaces of the device oriented toward the catheter entry site when the device is in use, may be referred to as the bottom of the device, regardless of the actual orientation of the device. Use of the words top and bottom, or any such directional terms, for other parts of the present device are to be interpreted in a manner consistent with the 'top' and 'bottom' of the cover, as defined above.

The term antimicrobial compound is used broadly herein to refer to any compound that achieves an antimicrobial effect in situ. Thus, the term may refer to compounds, such as antibiotics, that are directly antimicrobial in function, or to compounds such as hydrogen peroxide, which achieve an antimicrobial effect only by reaction with another compound (in the case of hydrogen peroxide, the enzyme catalase). Further, as defined herein, $O_2$ is considered an antimicrobial compound for purposes of the present invention, when present at sufficient concentration to have an antimicrobial effect. Antimicrobial compounds may also include oxidizing agents suitable for use in creating a vacuum. The form of the antimicrobial agent may be that of a liquid, gel, gas, or any other suitable form.

Figure 1:
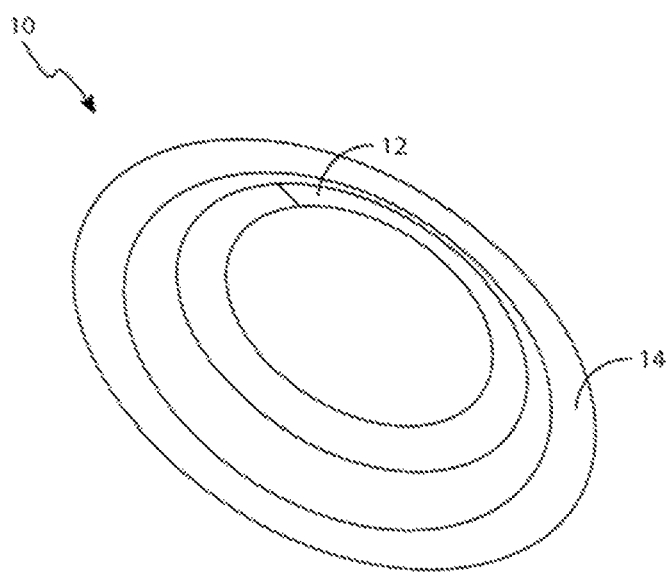
FIG. 1 is a top and side view of one embodiment of a portion of an antimicrobial catheter jacket.
Figure 2:
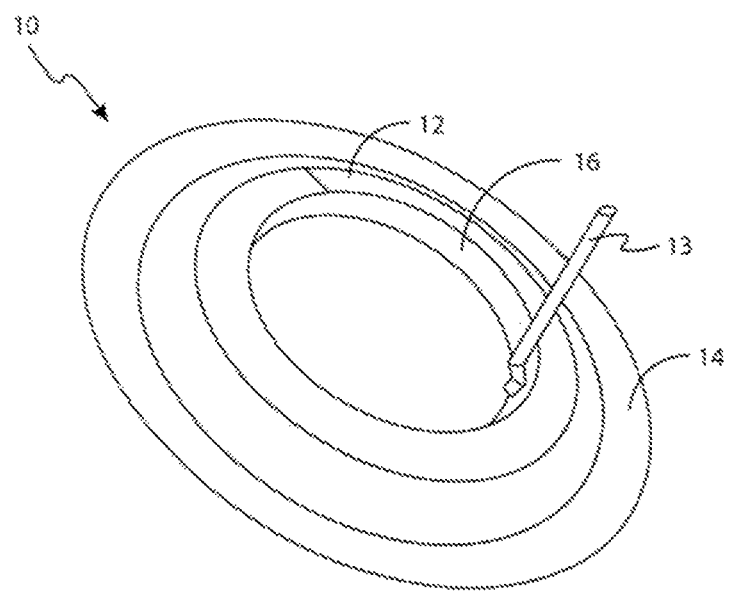
FIG. 2 is a perspective view of another embodiment of a portion of an antimicrobial catheter jacket.

Turning now to the drawings, wherein like numerals indicate like parts, FIG. 1 is a top and side view of a portion of one embodiment of an antimicrobial catheter jacket 10 of the present invention. In the embodiment of antimicrobial catheter jacket 10 shown in FIG. 1, a cover 12 is provided, cover 12 having an adhesive flange 14 extending around the perimeter thereof. Cover 12 is preferably constructed of a rigid or semi-rigid material, though any suitable material may be used in its construction. A dermal surface membrane 16 may be provided within cover 12, as best seen in FIG. 2. Cover 12 is open at the center thereof to allow a catheter to extend therethrough.

Dermal surface membrane 16 is constructed of a permeable material, and may be selectively permeable, semipermeable, or may allow any material therein to pass into the space between cover 12 and the point of entry of a catheter into the body. An inlet 13 may pass through cover 12, as shown in FIG. 2, and may be in fluid communication with the interior of dermal surface membrane 16, the inlet 13 allowing for introduction of various antimicrobial materials into dermal surface membrane 16. In the embodiment shown in FIG. 3, cover 12 also includes one or more outlets 15 that can be used to aspirate the interior of cover 12, drawing fluid or other materials out of cover 12 and away from the wound site. In some embodiments of the invention, outlets 15 may simply extend through cover 12 into the interior space thereof. In other embodiments of the invention, cover 12 may include a drainage structure 17, such as that shown in FIG. 3, having a plurality of openings therein, such that fluid or other material within the interior of cover 12 passes through the openings and into drainage structure 17. In embodiments wherein both outlets 15 and drainage structure 17 are used, outlets 15 may be in fluid communication with the interior of drainage structure 17 and can be used to aspirate material from the interior thereof. Outlets 15 are preferably accessible from the exterior of the device for aspiration.

Figure 3:
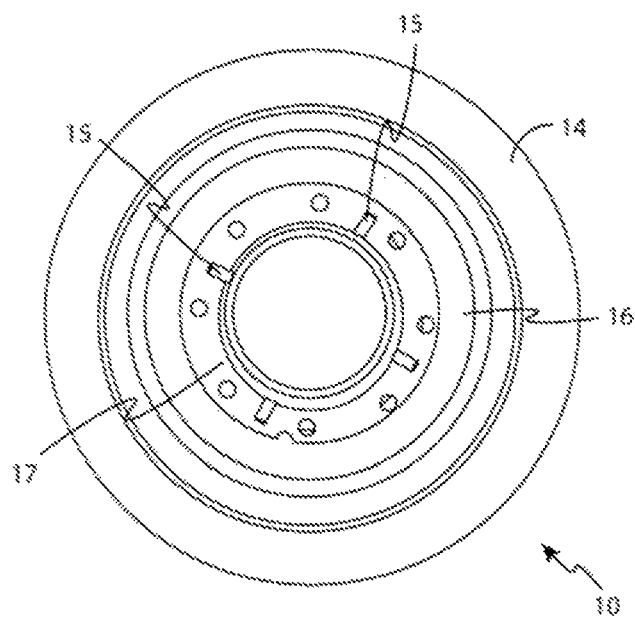
FIG. 3 is a bottom view of one embodiment of an antimicrobial catheter jacket.

Dermal surface membrane 16 may be provided as a single layer of membrane extending across a portion of the interior of cover 12, or maybe provided, as shown in FIGS. 2 and 3, as a tubular structure that extends along an inner circumference of cover 12. Inlet 13 is used to introduce an antimicrobial compound into dermal surface membrane 16, the membrane allowing the compound to move into the interior space of cover 12 over time, thereby coming in contact with the exterior of a catheter, as well as the dermal surface around the point of entry of the catheter into the patient's body. Any suitable antimicrobial compound, or combination of compounds, may be introduced into dermal surface membrane 16. For example, antibiotics may be used to kill bacteria at or near the wound site. Likewise, hydrogen peroxide may be used, the hydrogen peroxide reacting with the enzyme catalase present at the wound site to generate oxygen levels lethal to microorganisms. In some embodiments of the invention, oxygen gas may be introduced into the membrane, or compounds that produce oxygen gas may be utilized. In such embodiments, a hyperbaric oxygen environment may be created within cover 12, aiding in the elimination of microorganisms on the surface of a catheter and at or around the site of entry of the catheter into the body of a patient.

In the embodiment of antimicrobial catheter jacket 10 shown in FIGS. 1 through 3, for example, an adhesive flange 14 is provided to allow device 10 to adhere to the skin of a patient. The adhesive seal provided by adhesive flange 14 prevents the antimicrobial compounds introduced into cover 12 from leaking out of the device. Adhesives suitable for use in adhering a device such as antimicrobial catheter jacket 10 to a patient's skin are well known in the art. The adhesive may be applied to the bottom surface of adhesive flange 14, for example, and may be covered with a peelable strip to protect the adhesive until the device is ready for use. Flange 14 and cover 12 are flexible enough to allow flange 14 to conform to the skin of a patient at the site where the antimicrobial catheter jacket 10 is used. In embodiments of the present device wherein a vacuum or desired gaseous environment is maintained within said device, in order to inhibit microbial growth and promote healing, it is contemplated that the adhesive forms an airtight seal to the skin of the patient, that the present device itself is airtight in construction, and that the device forms an airtight connection with the hemodialysis catheter or other instrument where the device and the catheter or other instrument are in contact.

Outlets 15 and inlet 13 are sealed when not in use for aspiration or introduction of a compound into dermal surface membrane 16. Inlet 13 may be structured such that it is unidirectional, such as via a one-way valve or other structure, so that material introduced into dermal surface membrane 16 is unable to leak out through inlet 13. Alternatively, inlet 13 may be provided with a cap. Outlets 15 may be capped or may be sealed in such that manner that they remain closed unless a force, such as that generated by aspiration with a vacuum, forces material through the seal and allows the material to exit cover 12.

FIG. 3 shows a bottom view of antimicrobial catheter jacket 10. Outlets 15 are visible, as is drainage structure 17. Dermal surface membrane 16 is shown, as well as adhesive flange 14, which serves to hold the device firm against the skin of a patient.

Figure 4:
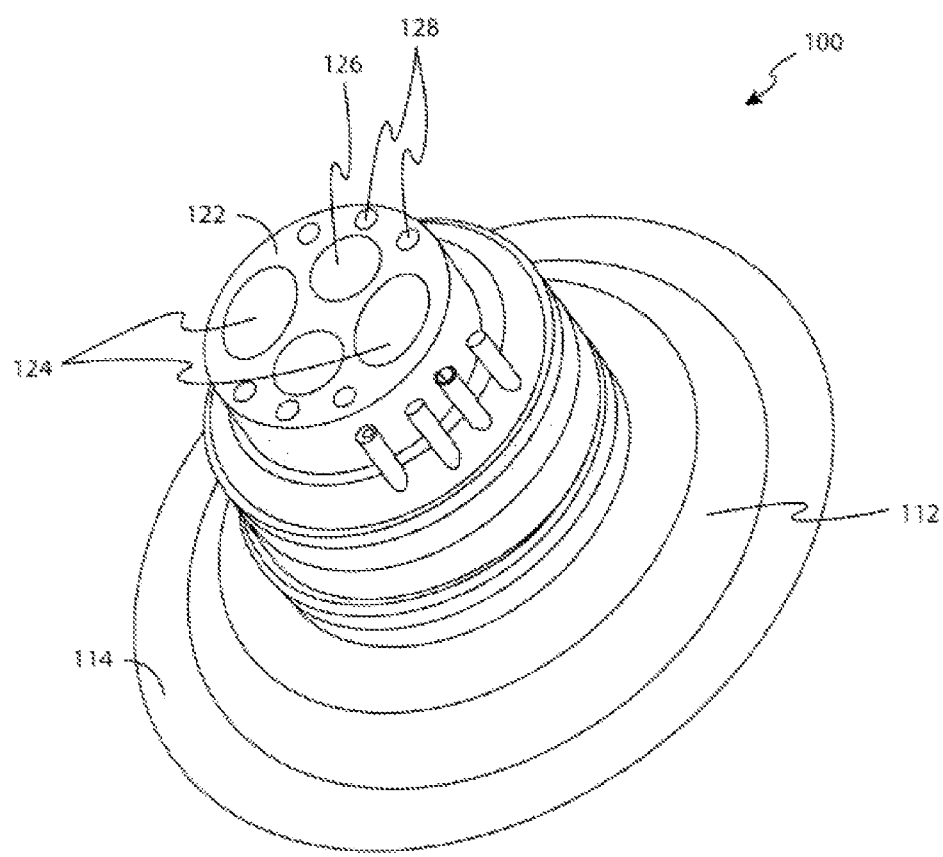
FIG. 4 is a top and side perspective view of one alternative embodiment of an antimicrobial catheter jacket having a hemodialysis catheter associated therewith.

FIG. 4 is a perspective view of an embodiment of antimicrobial catheter jacket 100 showing a hemodialysis catheter 122 associated therewith. Antimicrobial catheter jacket 100 includes a cover 112 with an adhesive flange 114 around the circumference thereof. Cover 112 is open at the center thereof to allow hemodialysis catheter 122 to extend through cover 112. In the embodiment of the antimicrobial catheter jacket shown in FIG. 4, a catheter surface membrane 118 is provided (best seen in FIG. 5), this membrane being in contact with the exterior surface of hemodialysis catheter 122. In the embodiment shown in FIGS. 4 and 5, catheter surface membrane 118 is preferably an annular tube that extends around the circumference of hemodialysis catheter 122. Catheter surface membrane 118 maybe be filled with any suitable antimicrobial compound, or combination of compounds, as described with respect to other embodiments, above, including oxygen-producing compounds, and the like. As hemodialysis catheter 122 passes through antimicrobial catheter jacket 100, the outer surface thereof contacts catheter surface membrane 118 prior to passing through the skin of a patient, thereby disinfecting the exterior of the catheter and reducing the risk of infection to the patient.

A catheter surface membrane inlet 130 (best shown in FIG. 7) is provided for the introduction of antimicrobial compounds, or other desirable compounds, into catheter surface membrane 118. Catheter surface membrane 118 is permeable (selectively, semi-permeable, or otherwise) so that the compound inserted thereinto can be passed from the membrane to the surface of hemodialysis catheter 122. Catheter surface membrane inlet 130 may be unidirectional, such as through a one-way valve, or may be sealed with a cap or other suitable structure so that a compound inserted into catheter surface membrane 118 via inlet 130 cannot leak out of the membrane through inlet 130.

Figure 5:
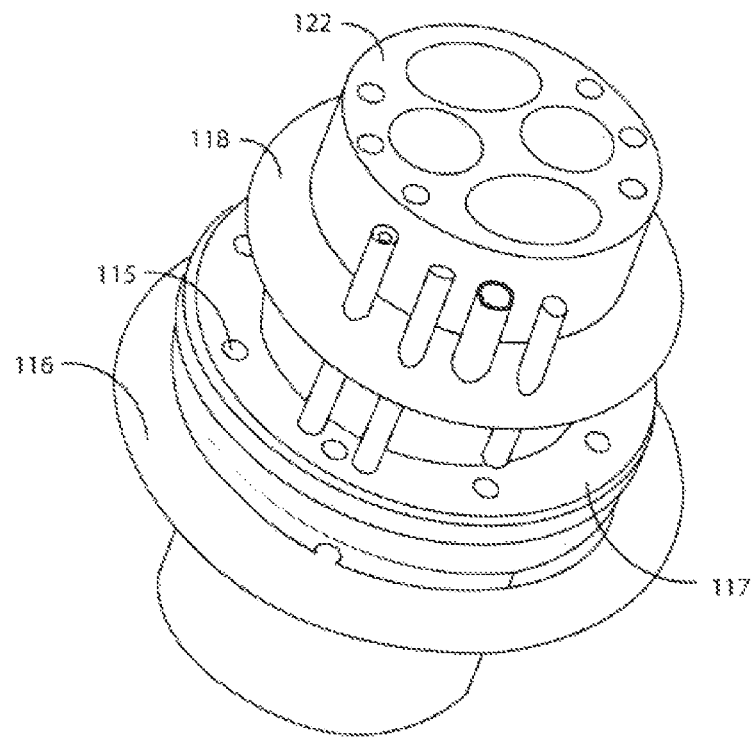
FIG. 5 is a top and side perspective view of portions of the interior structure of the embodiment of an antimicrobial catheter jacket depicted in FIG. 4.

FIG. 5 provides a perspective view of one embodiment of antimicrobial catheter jacket 100, with cover 112 removed to reveal portions of the interior structure thereof. Catheter surface membrane 118 is shown in contact with an exterior surface of hemodialysis catheter 122. A dermal surface membrane 116 is also shown, this membrane being located at or near the surface of the skin of the patient to whom antimicrobial catheter jacket 100 is being applied. Drainage structure 117 is also depicted. Drainage structure 117 has a plurality of aspiration outlets 115 through which material from within drainage structure 117 may be withdrawn. The lower surface of drainage structure 117, not visible in FIG. 6, includes a plurality of inlets, which allow material contained within cover 112 to enter into drainage structure 117. Various inlets are also provided so that compounds can be introduced into the membranes provided in antimicrobial catheter jacket 100, these inlets being described in greater detail, below. In addition to its function in drainage and aspiration of materials from within device 100, drainage structure 117 may also be provided in rigid or semi-rigid form to provide support for other structures of antimicrobial catheter jacket 100.

Figure 6:
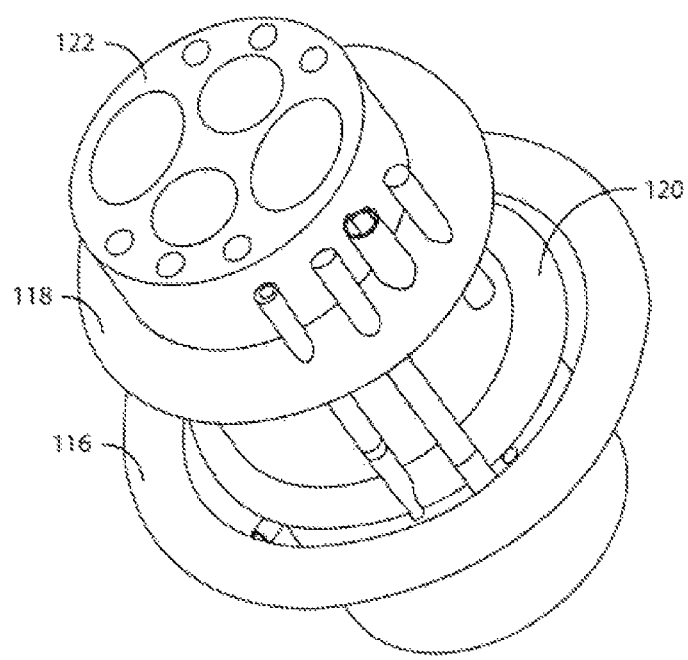
FIG. 6 is a top and side perspective view of portions of the interior structure of one embodiment of an antimicrobial catheter jacket.

A secondary catheter surface membrane 120 is shown in the embodiment of antimicrobial catheter jacket 100 depicted in FIG. 6. As shown, secondary catheter surface membrane 120 contacts the exterior surface of hemodialysis catheter 122, but may also be positioned sufficiently low to contact a patient's skin around the wound site where the catheter penetrates the skin. Secondary catheter surface membrane 120 may be provided in addition to, or in place of dermal surface membrane 116, to allow for introduction of antimicrobial material into cover 112 of antimicrobial catheter jacket 100. Various inlets shown in FIGS. 4 through 7 are described in detail below.

FIGS. 4 through 6 depict one embodiment of a hemodialysis catheter 122 suitable for use in the various embodiment of the present invention. Hemodialysis catheter 122 includes primary lumina 124 (labeled in FIG. 4), which function in a similar fashion as lumina in a traditional hemodialysis catheter in that they provide passages for blood flow into the patient's body, and removal of blood therefrom.

Also present are secondary lumina 126 (also labeled in FIG. 4). It is contemplated that secondary lumina 126 may be used to circulate a heated solution, such as water or saline, through the interior of the catheter in order to raise the temperature of the catheter to a level that is lethal to many microorganisms. Thus, the circulation of fluid through these lumina can provide an antimicrobial effect, while at the same time not raising the temperature enough to have a detrimental effect on the patient or on the blood blowing through the catheter.

Tertiary lumina 128 may be present, and may be provided in varying numbers, and offer additional options for achieving an antimicrobial effect in hemodialysis catheter 122. Tertiary lumina 128 may, for example contain heating elements (not shown) inserted therein, the heating elements serving to raise the temperature of hemodialysis catheter 122 to a level lethal to many microorganisms. These heating elements may be provided instead of, or in addition to, secondary lumina 126 having water or other solution flowing therethrough in order to regulate the temperature of hemodialysis catheter 122. The primary, secondary, and tertiary lumina are preferably physically separate from one another, and not in fluid communication with one another.

It should be noted that the present device provides a steady, continuous antimicrobial environment within the device or at the surface of the catheter or other device. This is in contrast to approaches that may provide an initial, strong peak of antimicrobial activity, but wherein the antimicrobial activity drops substantially immediately thereafter. Further, as described further elsewhere herein, it is contemplated that antimicrobial structures may be used in conjunction with the present device. Such antimicrobial structures may, for example, be placed within the structure of the device, and may include heating elements, ultraviolet sources, ultrasonic sources, and the like.

Figure 7:
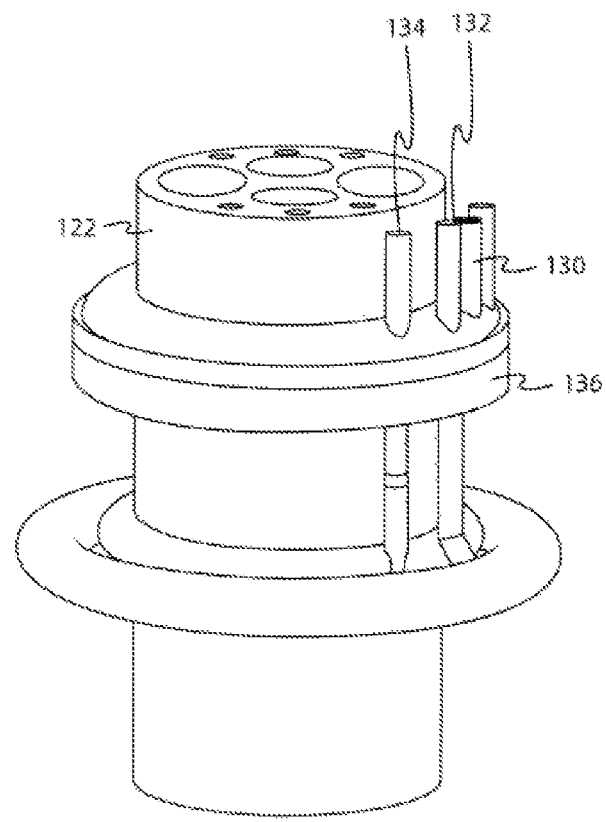
FIG. 7 is a side perspective view of portions of the interior structure of the embodiment of an antimicrobial catheter jacket depicted in FIG. 6.

FIG. 7 shows a perspective view of certain interior structures associated with an embodiment of the antimicrobial device of the present invention. Portions of the structure have been stripped away to allow view of inlets 130, 132, and 134. Each of these inlets may include a cap at the top opening thereof, or may include other sealing structures designed to maintain flow through the inlets in a single direction, and to prevent backward flow and leaking therefrom.

Catheter surface membrane inlet 130 extends from at or near the upper end of hemodialysis catheter 122 to catheter surface membrane 118. Dermal surface membrane inlet 132 extends from at or near the upper end of hemodialysis catheter 122 to dermal surface membrane 116. Secondary catheter surface membrane inlet 134 extends from at or near the upper end of hemodialysis catheter 122 to secondary catheter surface membrane 120.

The embodiment of the present invention shown in FIG. 7 further includes an antimicrobial source 136 around hemodialysis catheter 122. Antimicrobial source 136 may be, for example, a heating element designed to maintain hemodialysis catheter 122 at a temperature lethal to many microorganisms. Alternatively, antimicrobial source 136 may be a UV source adapted to irradiate the external surface of hemodialysis catheter 122 with UV light, thereby having an antimicrobial effect thereon. The use of UV radiation to achieve this effect is described in greater detail with respect to other embodiments of the invention, below.

Figure 8:
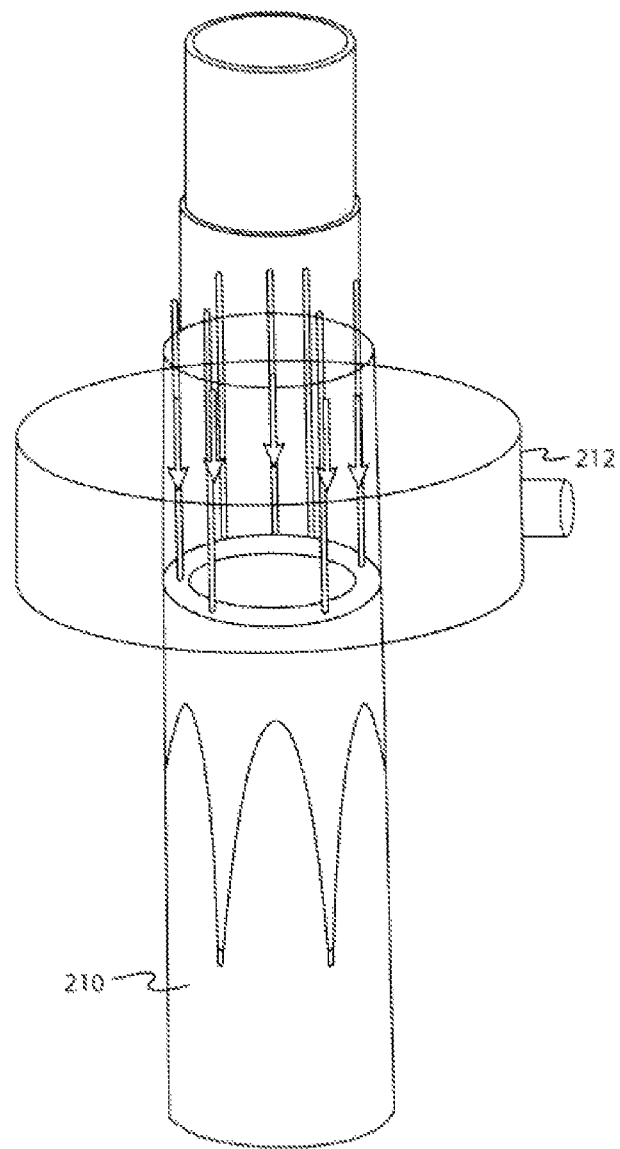
FIG. 8 depicts an alternative embodiment of an antimicrobial catheter jacket having a hemodialysis catheter extending therethrough.

FIG. 8 depicts one alternative embodiment of a antimicrobial catheter jacket. The numeral 210 refers generally to a hemodialysis catheter for use with the present device. An antimicrobial cover, referred to in this embodiment as an antimicrobial "jacket" 212 is provided around a portion of hemodialysis catheter 210, the jacket 212 having a central opening that allows a sliding engagement with hemodialysis catheter 210. Jacket 212 includes elements that reduce the microbial population on the outer surface of hemodialysis catheter 210.

Figure 9:
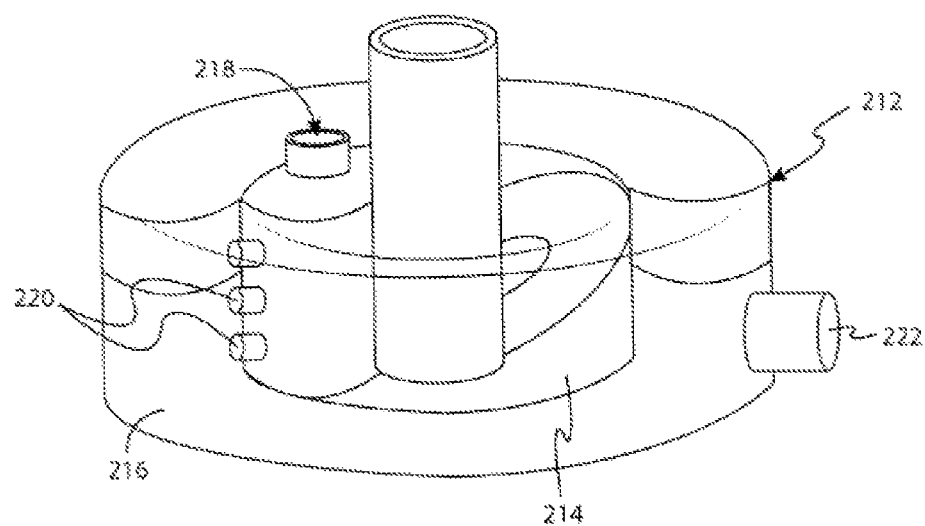
FIG. 9 depicts an alternative embodiment of an antimicrobial catheter jacket, the antimicrobial catheter jacket having an inner jacket and an outer jacket, and including structures for impacting the flow of antimicrobial compounds therethrough.

FIG. 9 depicts one embodiment of an antimicrobial catheter jacket of the present invention. The embodiment of the present device shown in FIG. 9 utilizes an antimicrobial gel or other compound that is able to flow through various compartments of the jacket. The embodiment of the present device shown in FIG. 9 includes an inner antimicrobial jacket 214 and an outer antimicrobial jacket 216. The inner and outer antimicrobial jackets include various one-way valves for introducing an antimicrobial compound into the jacket. Inner antimicrobial jacket 214 has a central opening at the top thereof, and another corresponding central opening at the bottom thereof. The hemodialysis catheter passes through these openings. The combination of inner jacket 214 and outer jacket 216 form a single, larger antimicrobial jacket 212.

Inner jacket 214 includes an injection port 218, via which an antimicrobial compound may be introduced into inner jacket 214. Injection port 218 preferably includes a one-way valve so that the antimicrobial compounds cannot flow out of inner jacket 214 through injection port 218. Hemodialysis catheter 210 extends through the top and bottom openings in inner jacket 214 and is exposed to the interior of inner jacket 214. Thus, the outer surface of hemodialysis catheter 210 contained within inner jacket 214 is contacted by the antimicrobial compound. Seals may be provided to prevent the antimicrobial compounds from leaking out through the top and bottom openings of inner jacket 214.

As an alternative to the surface of hemodialysis catheter 210 being exposed to the interior of inner jacket 214, it is contemplated that the interior of inner jacket may be constructed from a semipermeable material, thereby allowing an antimicrobial agent within inner jacket 214 to be introduced onto the surface of hemodialysis catheter 210.

Once within inner jacket 214, the antimicrobial compound comes into contact with the outer surface of the portion of hemodialysis catheter 210 extending through inner jacket 214. As noted above, injection port 218 includes a one-way valve so that the antimicrobial compounds cannot leave inner jacket 214 via that port. It is desirable, however, to maintain a flow of the antimicrobial compound through inner jacket 214 in order to maintain the greatest efficacy of antimicrobial activity. Outlet valves 220 are provided along a surface of inner jacket 214 to allow the flow of antimicrobial compounds from inner jacket 214 into outer jacket 216. Although three outlet valves 220 are shown in the Figure, it is contemplated that any suitable number of outlet valves 220 may be employed, including a single outlet valve 220. As with injection port 218, outlet valves 220 are preferably one-way valves so that antimicrobial compound does not flow from outer jacket 216 back into inner jacket 214.

Both inner jacket 214 and outer jacket 216 may include internal structures (detailed below, and best shown in FIG. 12) designed to aid the flow of antimicrobial compound through the device. Preferably, the flow of antimicrobial compound is such that a lower pressure of antimicrobial compound exists in outer jacket 216 as compared to inner jacket 214. This "pulls" the antimicrobial compound from inner jacket 214, through outlet valves 220, and into outer jacket 216. Outer jacket 216 also includes an ejection port 222 via which the antimicrobial compound flows out of outer jacket 216.

In some embodiments of the invention, it is contemplated that a constant supply of antimicrobial compound will be introduced into the present device via injection port 218. A reservoir (not shown) containing antimicrobial compound may be provided in fluid communication with inner jacket 214 via injection port 218, and the pressure of the constant supply of antimicrobial compound into inner jacket 214 acts to force the antimicrobial compound to flow through the device. Ejection port 222 may be in communication with a second reservoir (not shown) for receiving the antimicrobial fluid as it leaves the present device. The receiving reservoir may simply passively receive the antimicrobial compound, or a pump or other mechanism may be provided to pull the antimicrobial compound through the device.

Although the embodiment of the present device described above includes a reservoir from which antimicrobial compound is introduced into inner jacket 214 and a reservoir into which antimicrobial compound is ejected from outer jacket 216, it is contemplated that in some embodiments of the present invention, antimicrobial compound may simply be recirculated within the device. In such embodiments, ejection port 222 and injection port 218 are in fluid communication, and a pump or other mechanism is provided to maintain the flow of antimicrobial compound through the device. Even without introduction of fresh antimicrobial compound into the system, the flowing action of the antimicrobial compound through inner jacket 214 and outer jacket 216 will have an efficacious effect, and ensures that the antimicrobial compound is mixed as it flows through the device, such that the same portion of the antimicrobial compound is not continuously in contact with the surface of hemodialysis catheter 210.

Figure 10:
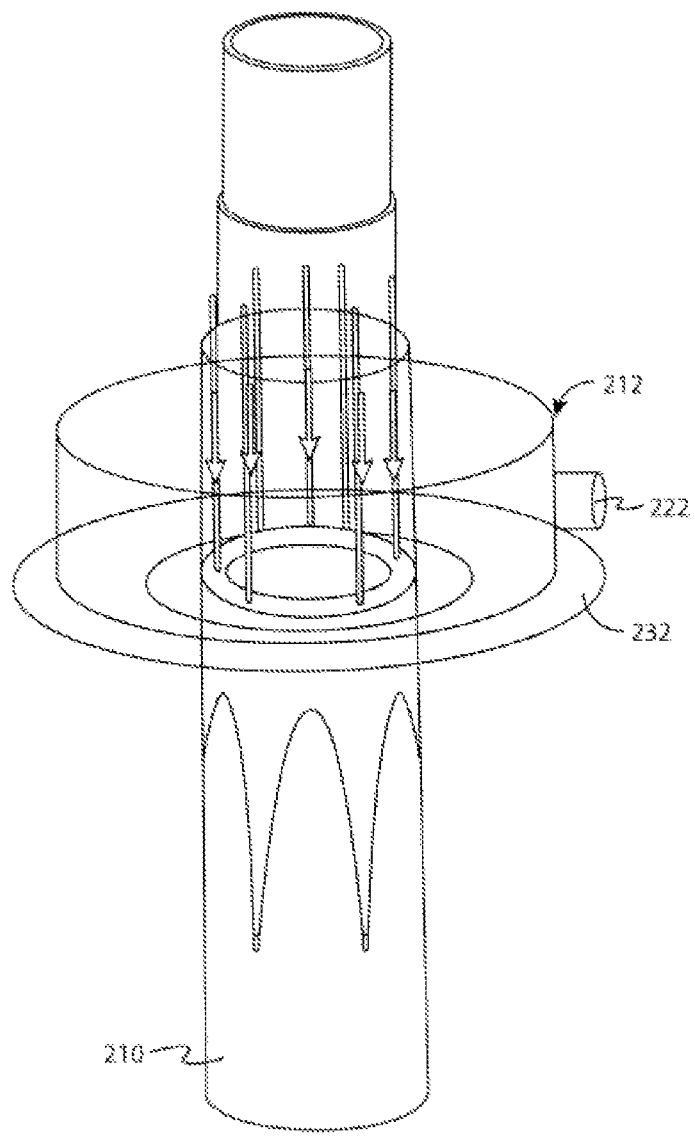
FIG. 10 depicts an alternative embodiment of an antimicrobial catheter jacket having an adhesive seal.

As shown in FIG. 10, other embodiments of the present device may include an adhesive seal 232. The adhesive seal 232 is used to firmly affix antimicrobial jacket 212 (which may, in some embodiments, comprise an inner jacket 214 and an outer jacket 216) to the skin of a patient receiving a hemodialysis catheter. This prevents unwanted movement of jacket 212 while the device is in use, and can also help secure hemodialysis catheter 210. Adhesive seal 232 may be formed as an integral part of jacket 212, with that portion that forms the adhesive seal being the only surface that receives an adhesive. Alternatively the entire underside of jacket 212, including a flange portion extending therearound, may receive an adhesive for affixing the device to the skin of a patient. It is preferred that prior to application of jacket 212 onto the skin of an individual, the portion of jacket 212 containing the adhesive be protected by cellophane or any suitable peelable protecting surface or film. This can be peeled back immediately prior to application onto the skin of a patient, thereby exposing the surface of the adhesive.

Figure 11:
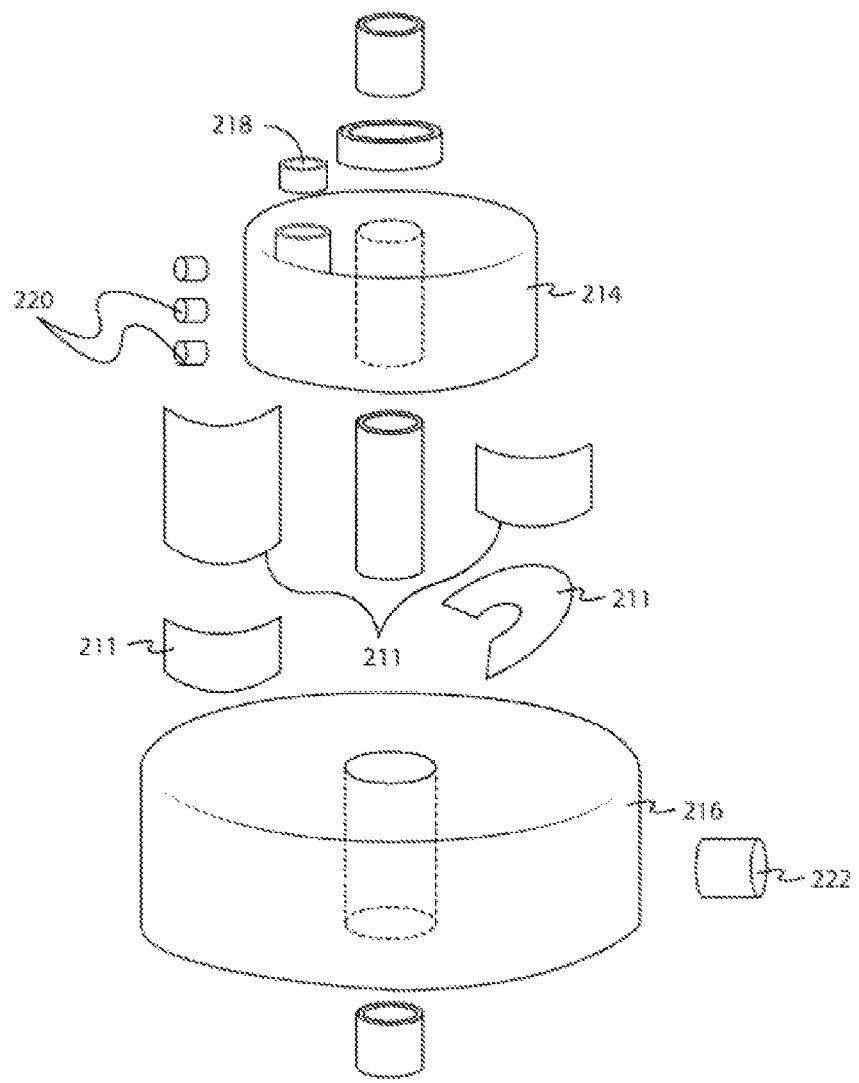
FIG. 11 is an exploded view of an alternative embodiment of an antimicrobial catheter jacket

FIG. 11 is an exploded view showing one embodiment of the present invention, including inner jacket 214 and outer jacket 216 which, in this embodiment, include structural components designed to impact the flow of antimicrobial gel or fluid therethrough. For example, inner antimicrobial jacket 214 may include a variety of differently shaped modular trusses 211 for directing the flow of antimicrobial gel or other fluid therethrough. It is preferred that these modulating trusses are sized, shaped, and positioned to direct the flow of antimicrobial get such that the pressure of the gel, as well as the contact of the gel with the hemodialysis catheter and the skin of the patient, is maximized. Outer jacket 216 may, likewise, include modulating trusses 21. It is preferred that the trusses contained within the outer jacket 216 are sized, shaped, and positioned to increase the contact pressure of the antimicrobial gel within the outer chamber, but to ensure that the pressure of the gel within outer chamber 216 is lower than within inner jacket 214 so that there is no retrograde flow of gel from outer jacket 216 to inner jacket 214. The other elements of the device shown in FIG. 11 are as described with respect to previous embodiments, above.

In one alternative embodiment of the invention, jacket 212 includes a UV source for generating UV radiation. It is contemplated that the wavelength of the UV radiation utilized is within a range effective for killing microorganisms (for example, a wavelength around 254 nm is generally considered effective). If desired, the UV source may be adapted to cycle through a variety of wavelengths, where each individual wavelength is most effective against certain microorganisms.

The UV source is preferably disposed circumferentially around opening 224, through which hemodialysis catheter 210 is extended, in a similar manner as element 136 shown in the embodiment of the present invention depicted in FIG. 8. Thus, the UV radiation generated by the UV source impacts the surface of hemodialysis catheter 210 fully around an outer perimeter thereof.

In embodiments of the present invention wherein a UV source is utilized, it is contemplated that the portion of jacket 212 extending from the UV source to the surface of the hemodialysis catheter is constructed of a material that allows transmission of UV light. The outer surface of jacket 212 may be constructed of a separate material, preferably one that is impermeable to UV light, so that the UV radiation generated by the UV source is not lost through the exterior of jacket 212. The inner surface of the outer surface or coating of jacket 212 may be also be capable of reflecting UV radiation back to the interior of jacket 212 (i.e. toward the surface of hemodialysis catheter 10).

In some embodiments of the invention, rather than jacket 212 being comprised of a solid material capable of transmitting UV radiation, the interior of jacket 212 may be hollow, with openings in the top and bottom surface thereof firmly holding hemodialysis catheter 210 in place while the exterior surface thereof is being irradiated. In still other embodiments of the invention, jacket 212 may be made smaller in diameter, such that the UV source is positioned in close proximity to the exterior surface of hemodialysis catheter 210 and transmits UV radiation directly thereto. Even if the larger dimensions of jacket 212 are retained, the UV source may be positioned in close proximity to hemodialysis catheter 10.

In any of the above embodiments of the invention utilizing a UV source, it is contemplated that the UV radiation from the UV source effectively sterilizes the outer surface of hemodialysis catheter 210, destroying microbes thereon that may pose a risk of infection to the patient. If hemodialysis catheter 210 is being inserted through jacket 212 and then introduced into the body of a patient, the rate of movement of hemodialysis catheter 210 through jacket 212 may be adjusted to optimize the length of time for which any given portion of the surface of hemodialysis catheter 210 is exposed to the UV radiation. It is contemplated that variations in the wavelength of UV radiation used, as well as in the length of time any given portion of hemodialysis catheter 210 is exposed to the UV radiation, are well within the ordinary skill in the art. A user of the present invention having ordinary skill in the art will, upon reading this disclosure, be able to determine the optimum conditions for any given use of the present invention.

In still another embodiment of the invention, jacket 212 includes a heating element or other heat source to allow the present device to regulate the temperature of the surface of hemodialysis catheter 210. In such embodiments, jacket 212 is preferably constructed of a thermal-conductive material that allows the heat generated by the heating element to be distributed along the surface of hemodialysis catheter 10 when the hemodialysis catheter is inserted into jacket 212.

In embodiments of the invention employing a heating element, it is contemplated that the temperature at the surface of hemodialysis catheter 210 may be optimized to destroy microbes on the surface thereof that are sensitive to changes in temperature. It is contemplated, however, that the temperatures utilized by the device are not harmful to the body or to blood flowing through hemodialysis catheter 210. In some situations, it may also be necessary to take into account pharmaceuticals being taken by the patient, so that the temperature of hemodialysis catheter 210 is not raised to a level that will cause degradation of the pharmaceuticals or otherwise render them ineffective. Such determinations will be within the capabilities of one of skill in the art upon reading this disclosure.

In embodiments of the invention such as those described above, having features such as a UV source or heating element, a power source is required to provide the desired functionality to the device. It is preferred that a battery be provided to power such components, though it is possible that the present device may be adapted to plug into a standard wall socket for the purpose of receiving power. In embodiments wherein a battery is utilized, the present device may include standard batteries that are removed when depleted and replaced with new batteries, or may utilize rechargeable batteries. In embodiments of the present invention wherein rechargeable batteries are used, a charging port is also provided. The charging port may be any suitable port for connecting to an adapter that is plugged into a wall socket or other power source.

In some of the embodiments of the present invention wherein antimicrobial gels or other fluids are utilized, it is contemplated that the side of the present device that contacts the skin of a patient when the device is in use may be open to the skin in the area of inner jacket 214. Thus, instead of inner jacket 214 having an upper surface and a lower surface (using the perspective shown in the drawings) such that the antimicrobial gel is contained between these two surfaces, inner jacket 214 has an upper surface and the skin of a patient forms the lower barrier of inner jacket 214. This embodiment provides the benefit of exposing a larger portion of the skin around the insertion side of hemodialysis catheter 210 to the circulating antimicrobial gel within inner jacket 214. As the antimicrobial gel travels through the present device, it not only kills microorganisms on the surface of the hemodialysis catheter, but also on the surface of the patient's skin. This can be important because *S. aureus*, a major source of infection for patient's with a hemodialysis catheter, is commonly found on the human skin.

Figure 12:
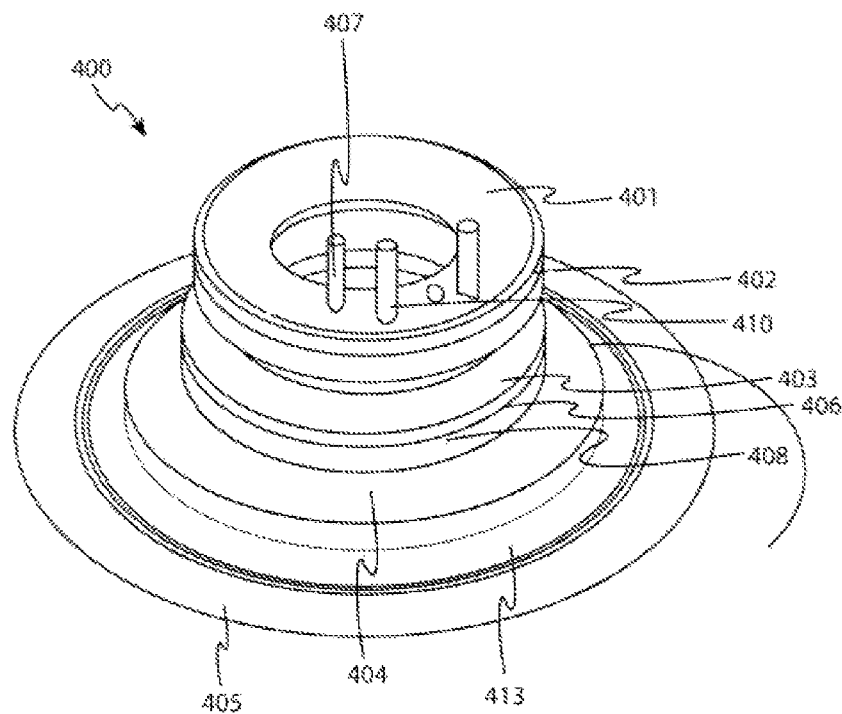
FIG. 12 is a perspective view of an alternative embodiment of an antimicrobial catheter jacket.

FIG. 12 provides a perspective view of another embodiment of an antimicrobial catheter jacket. Wound care device 400 is configured to be placed around the site of a catheter inserted into the skin of a patient and has a central opening for insertion of a catheter therethrough. When properly placed, antimicrobial catheter jacket 400 reduces or eliminates extra-luminal infections associated with the use of the catheter, and with movement of the catheter in and out of the insertion site. A reservoir 401 is provided, the reservoir constructed of a material having elastic or stretchable properties and which is impervious to the flow of liquids or gasses. The elasticity of the material from which reservoir 401 is constructed allows the reservoir to be filled using a syringe or other suitable mechanism, to maintain a positive pressure for flow out an antimicrobial agent out of reservoir 401. Inlet 407 allows introduction of antimicrobial agents into reservoir 401, and preferably includes a one-way valve that prevents flow of the antimicrobial agent out of reservoir 401 via inlet 407. First housing 402 provides structural support for antimicrobial catheter jacket 400 and various components thereof. A second housing 414 may be provided in some embodiments of the device (see FIG. 13, below) for additional support or to accommodate additional structure of device 400. Additional housings may be provided as necessary or desired. Effluent reservoir 403 is provided for collection of effluent around the catheter. Outlet 410 provides access to effluent reservoir 403 for removal of collected effluent therefrom. A flange 405 forms a base of antimicrobial catheter jacket 400. Flange 405 can conform to the skin of a patient using antimicrobial catheter jacket 400, and may include an adhesive such that antimicrobial catheter jacket 400 is firmly adhered to the patient's skin and a seal is formed to contain the antimicrobial agent at the site of the wound (i.e. the insertion site of the catheter).

Figure 13:
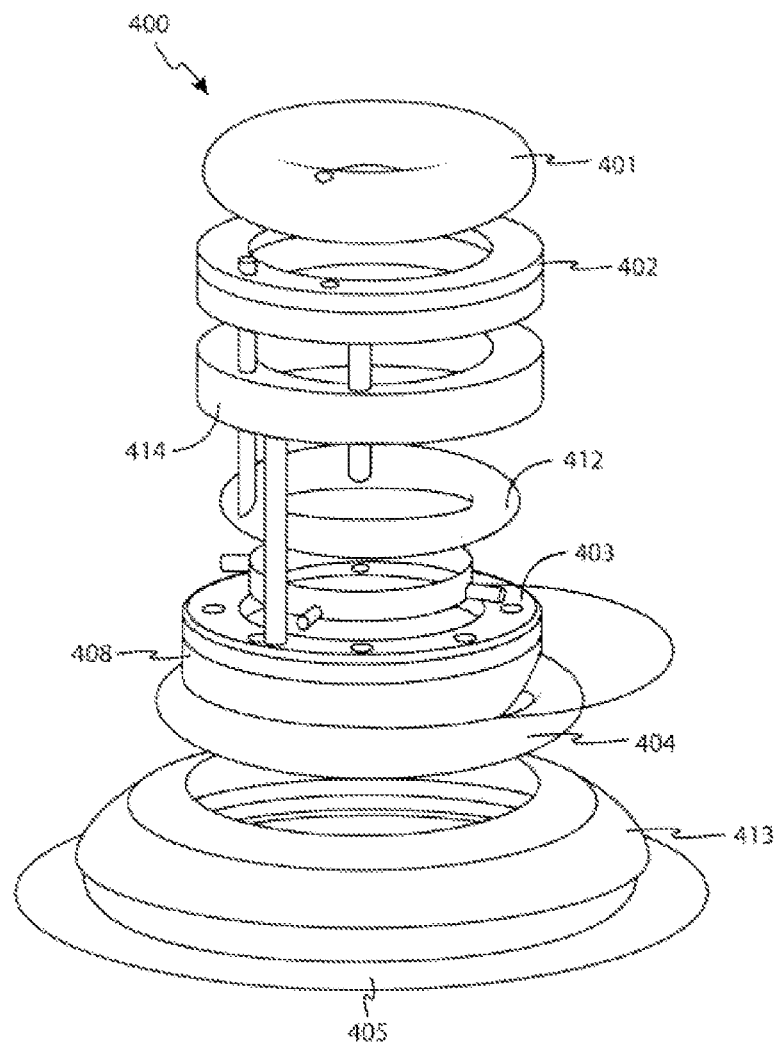
FIG. 13 is an exploded view of an antimicrobial catheter jacket.

FIG. 13 provides an exploded view of antimicrobial catheter jacket 400 having a second housing 414. Various other components of the antimicrobial catheter jacket 400 shown in FIG. 13 are described above.

The various components of the embodiments described above and shown in the drawings may be connected in any suitable manner. Some components, such as conduits and membranes, are in fluid communication, and may be provided as single, contiguous portions of material or may be multiple portions of material attached by adhesives, heat, or other known processed. Components not in fluid communication may likewise be manufactured as single pieces, attached by adhesives, heat processes, and so on. It is contemplated that various methods or processes for attaching the components of the present device are well known in the art.

The foregoing descriptive and accompanying illustrations are intended to be exemplary of the principles of the present invention. Various modifications to the description provided herein will be readily apparent to one of ordinary skill in the art upon reading this disclosure, and it is contemplated that such modifications are within the spirit and scope of the present invention.

Having thus described the preferred embodiment of the invention, what is claimed as new and desired to be protected by Letters Patent includes the following:

1. An antimicrobial device for use with a catheter, the device comprising:
   a jacket having a central opening in a surface thereof, the central opening sized and shaped to receive a catheter in sliding engagement therewith;
   an antimicrobial compound disposed within said jacket for reducing the number of microbes on the exterior surface of the catheter, wherein the antimicrobial means is selected from the group consisting of a liquid, a gel, gas, or combinations thereof; and a truss disposed within said jacket to direct the flow of said antimicrobial compound, wherein when the catheter is inserted through the central opening of the jacket, the antimicrobial compound contacts the exterior surface of the catheter within the jacket.

2. The antimicrobial device of claim 1, wherein a surface of the antimicrobial device contacting the skin of a patient when the antimicrobial device is in use comprises an adhesive to firmly affix the antimicrobial device to the skin of the patient.

3. The antimicrobial device of claim 1, wherein the jacket further comprises:

an injection port adapted to allow said antimicrobial compound to flow into said jacket and to prevent said antimicrobial compound from flowing out of the jacket therethrough; and an ejection port allowing the antimicrobial compound to flow from said jacket.

4. The antimicrobial device of claim 1 wherein the jacket comprises:

an inner jacket defining a central opening therein sized and shaped to receive a catheter in sliding engagement therewith; and an outer jacket extending around said inner jacket, wherein the inner jacket comprises an injection port to allow said antimicrobial compound to flow into the inner jacket and at least one one-way valve extending from the inner jacket to the outer jacket to allow said antimicrobial compound to flow from the inner jacket to the outer jacket, and further wherein the outer jacket comprises an ejection port to allow said antimicrobial fluid to flow therefrom.

5. The antimicrobial device according to claim 4 wherein said truss is a first truss disposed within the inner jacket, and further wherein the first truss is configured to direct said antimicrobial compound toward the exterior surface of the catheter.

6. The antimicrobial device of claim 5 wherein the outer jacket comprises a second truss, and further wherein the second truss is configured to direct the flow of antimicrobial compound such that the pressure of such compound is lower within the outer jacket than the inner jacket.

7. The antimicrobial device of claim 6 further comprising a flange extending along a perimeter of said outer jacket, the flange comprising an adhesive for affixing the antimicrobial device to the skin of a patient.

8. An antimicrobial device for use with a catheter, the device comprising:

an inner jacket defining a central opening therein sized and shaped to receive a catheter therethrough, wherein the inner jacket comprises an injection port to allow an antimicrobial compound to be introduced thereinto;

an outer jacket extending around said inner jacket and in fluid communication with the inner jacket, wherein the outer jacket comprises an ejection port to allow said antimicrobial compound to flow therefrom, wherein the antimicrobial compound within the inner jacket contacts that portion of a catheter within said inner jacket when said catheter is inserted through said central opening.

9. The antimicrobial device according to claim 8 wherein the antimicrobial compound within the inner jacket is maintained at a greater pressure than the antimicrobial compound within the outer jacket, such that said antimicrobial compound tends to flow from said inner jacket to said outer jacket.

* * * * *